(12) United States Patent
Carle et al.

(10) Patent No.: US 9,149,430 B2
(45) Date of Patent: Oct. 6, 2015

(54) COMPOSITIONS COMPRISING CAROTENOIDS

(75) Inventors: Reinhold Carle, Altenriet (DE);
Andreas Schieber, Stuttgart (DE);
Susanne Mutter, Stuttgart (DE)

(73) Assignee: DSM IP ASSETS B.V., Heerlen (NL)

( * ) Notice: Subject to any disclaimer, the term of this patent is extended or adjusted under 35 U.S.C. 154(b) by 607 days.

(21) Appl. No.: 12/385,523

(22) Filed: Apr. 10, 2009

(65) Prior Publication Data
US 2009/0203799 A1   Aug. 13, 2009

Related U.S. Application Data

(63) Continuation of application No. 10/543,058, filed as application No. PCT/EP2004/000590 on Jan. 24, 2004, now abandoned.

(30) Foreign Application Priority Data

Jan. 31, 2003   (DE) .................................. 103 04 100

(51) Int. Cl.
| | | |
|---|---|---|
| *A61K 31/015* | (2006.01) | |
| *A61K 31/122* | (2006.01) | |
| *A61P 35/00* | (2006.01) | |
| *A61K 9/00* | (2006.01) | |
| *A23L 1/00* | (2006.01) | |
| *A23L 1/0524* | (2006.01) | |
| *A23L 1/275* | (2006.01) | |
| *A23L 2/02* | (2006.01) | |
| *A61K 9/16* | (2006.01) | |
| *A61K 47/36* | (2006.01) | |

(52) U.S. Cl.
CPC ............ *A61K 9/0095* (2013.01); *A23L 1/0029* (2013.01); *A23L 1/0524* (2013.01); *A23L 1/2753* (2013.01); *A23L 2/02* (2013.01); *A61K 9/1652* (2013.01); *A61K 47/36* (2013.01); *A23V 2002/00* (2013.01)

(58) Field of Classification Search
USPC ........................................................ 424/490
See application file for complete search history.

(56) References Cited

U.S. PATENT DOCUMENTS

| | | | |
|---|---|---|---|
| 2,373,729 A * | 4/1945 | Willaman ...................... | 516/105 |
| 3,595,676 A | 7/1971 | Langen et al. | |
| 4,519,961 A | 5/1985 | Schumacher et al. | |
| 5,952,295 A | 9/1999 | Arnaud-Battandier et al. | |
| 6,007,856 A | 12/1999 | Cox et al. | |
| 6,328,995 B1 | 12/2001 | Bewert et al. | |
| 6,436,461 B1 | 8/2002 | Bouwmeesters et al. | |
| 6,471,969 B1 * | 10/2002 | Schlachter et al. ............ | 424/400 |
| 2001/0027216 A1 * | 10/2001 | Levy et al. ..................... | 514/683 |
| 2004/0170693 A1 * | 9/2004 | Pedersen et al. .............. | 424/490 |

FOREIGN PATENT DOCUMENTS

| | | | | |
|---|---|---|---|---|
| FR | 2769837 | * | 4/1999 | ............... A61K 7/48 |
| JP | 2002-191295 | | 7/2002 | |
| JP | 2009-79052 A | | 4/2009 | |
| WO | WO 91/06292 | | 5/1991 | |
| WO | WO 99/20242 | | 4/1999 | |
| WO | WO 00/70967 | | 11/2000 | |
| WO | WO 02/094982 A2 | | 11/2002 | |
| WO | WO 03/015537 | | 2/2003 | |
| WO | WO 03/018186 | | 3/2003 | |

OTHER PUBLICATIONS

Chow et al., "Phytosterol Biosynthesis in Ripening Tomatoes", Journal of Food Science 1978:43(5);1424-1426.*
Boyle & Anderson, "A comparison of saturated and unsaturated fatty acids in dietary fats and oils." Personal Nutrition, 6th edition, Thomson/Wadsorth, 2007.*
Zitco et al, "Fraction of pectins form sunflowers, sugar beets, apples, and citrus fruits", Canadian Journal of Chemistry 1956:43(12);3206-3214.

* cited by examiner

*Primary Examiner* — Walter Webb
(74) *Attorney, Agent, or Firm* — Nixon & Vanderhye P.C.

(57) ABSTRACT

A novel composition for delivering carotenoids (e.g. α- and β-carotene, lycopene) and/or other physiologically active ingredients to the colon of humans after ingestion and for producing liquid food compositions insusceptible to polyphenol-protein reactions can be obtained by encapsulating said active ingredients with pectin, in particular with low-methoxylated pectin.

10 Claims, 1 Drawing Sheet

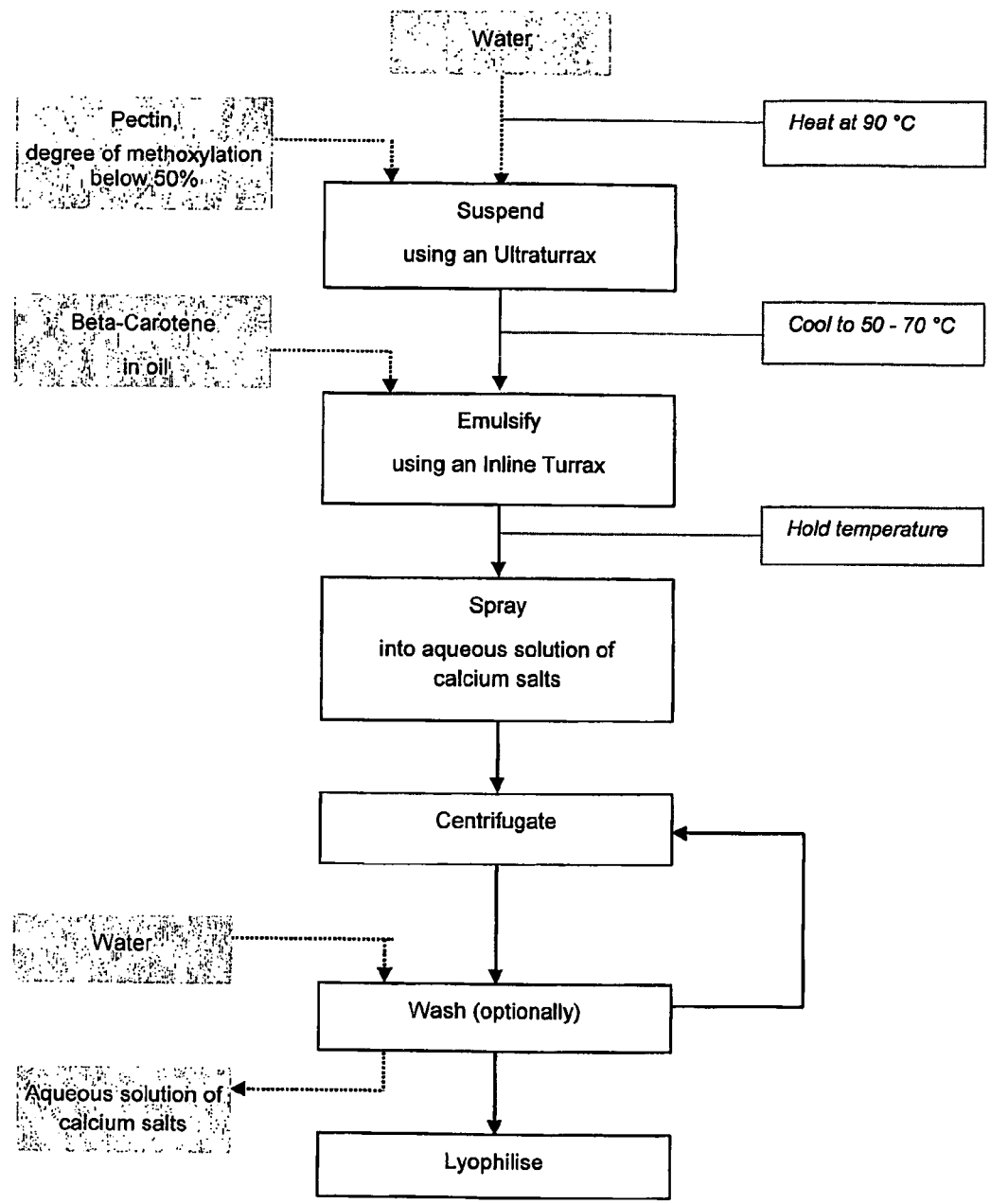

COMPOSITIONS COMPRISING CAROTENOIDS

This application is a continuation of U.S. Ser. No. 10/543,058 filed Jul. 21, 2005 now abandoned, which in turn is the US national phase of international application PCT/EP2004/000590 filed 24 Jan. 2004 which designated the U.S. and claims benefit of DE 103 04 100.1, dated 31 Jan. 2003, the entire content of which is hereby incorporated by reference.

The present invention relates to novel compositions comprising carotenoids and/or other physiologically active ingredients, in particular in encapsulated form, to food items comprising such composition, and to a process for their preparation.

Carotenoids have been reported to have beneficial effects on health. For example carotenoids such as β-carotene are thought to have an effect against colon carcinomas. It is believed that in order to have maximum beneficial effect, the carotenoids should be in such a (physical) form that they pass the stomach and small intestine without degradation or absorption, as it is believed to be desired for the effect on the colon that the carotenoids are available in the colon.

DE 19962427 discloses encapsulated bioactive components. The bioactive components that are mentioned are microorganisms with probiotic activity. The covering agent consists of non-digestible fibrous material. Examples given are: insoluble polysaccharides such as pectin, lignin, vegetable gums, but also soluble polysaccharides such as complex carbohydrates (e.g. fructo- or galactooligosaccharides, beta-glucans, etcetera). Example 6 mentions the use of a combination of pectin and inulin for encapsulating *Lactobacillus acidophilus*.

U.S. Pat. No. 5,356,636 describes the preparation of vitamin or carotenoid products in powder form by preparing an aqueous dispersion of the vitamins and carotenoids concerned and film-forming colloids and reducing sugars, converting this dispersion into powder from, and thermally treating the powder. The gelatin is used in combination with organic amino compounds. The content of carotenoids is generally 5-50%.

U.S. Pat. No. 4,389,419 discloses a process for encapsulating oils and oil-soluble substances (e.g. vitamin A) in microcapsules. The microcapsules are a shape-retaining alginate matrix filled with a precipitated polysaccharide and enclosing oil droplets.

EP 326026 discloses a method for reducing the oxidation of vitamins by combining the vitamins with triglycerides, complexing agents and covering agents, and optionally antioxidants. The covering agents disclosed are proteins, sugars, polysaccharides such as gum arabicum or starch.

EP 986963 describes a method for the production of a light- and oxidation-stable lycopene in the form of a dry powder. Said stability is achieved by having at least 20% of the lycopene in a crystalline form.

U.S. Pat. No. 5,780,056 discloses microcapsules comprising a carotenoid and an edible oil. The coating material is based on gelatin. The microcapsules prevent the carotenoid from oxidation.

WO 91/06292 discloses a method for the production of water-dispersible microparticles containing e.g. carotenoids. The microparticles are prepared by a specific process involving milling in water with a hydrocolloid. The hydrocolloid is reported to be gelatin, gum arabicum, protein or starch.

DE 19637517 reports a method for preparing a particulate cold-water dispersible carotenoid preparation. This is achieved by making a dispersion of carotene, optionally oil and/or emulsifier, in an organic solvent, which dispersion is mixed with an aqueous solution of a colloid such as gelatin, starch, dextrin, vegetable protein, pectin, gum arabicum, casein.

Although the methods as reported may be suitable for some purposes, it was desirable to have an alternative and improved preparation comprising carotenoids, which preparation should be such that the carotenoids are released in the colon, and not or to a limited extent only in the intestinal tract preceding the colon. Although β-carotene may be the preferred active ingredient, the invention is also applicable to other carotenoids and to other physiologically active compounds, respectively.

In accordance with the present invention It has been found that the above objectives may be achieved by an edible composition comprising at least 25% by weight, preferably at least 50% by weight, most preferably about 75% by weight of a pectin, particularly a pectin which gelatinizes by ionotropic gel formation, and at least 0.2% by weight of a carotenoid and/or another physiologically active ingredient, said percentages being based on the dry weight of the total composition.

Thus, in one aspect, the present invention relates to an edible composition comprising at least 25% by weight (based on the dry weight of the total composition) of a pectin, particularly a pectin which gelatinizes by ionotropic gel formation, and at least 0.2% by weight (based on the dry weight of the total composition) of a carotenoid and/or another active ingredient.

The pectin which gelatinizes by ionotropic gel formation is typically a pectin having a degree of esterification below 50% which is also referred to as low methoxylated pectin. Preferred pectins for use in the present invention are those having a degree of esterification between about 30 and about 45% and comprise about 70 to 90% of galacturonic acid units. The low methoxylated pectin may be an apple pectin or a citrus pectin whereas beet pectins are unsuitable for inotropic gel formation.

Such compositions can suitably be in the form of a particulate matter, preferably a dry particulate matter.

In a further aspect, the present invention relates to a process for the preparation of a composition comprising a carotenoid or mixture of carotenoids, and/or other active ingredients, which process includes the following steps:

a) prepare an aqueous suspension comprising a pectin, particularly a pectin which gelatinizes by ionotropic gel formation,
b) add a composition comprising at least 0.5% by weight (based on the dry weight of the final composition) of a carotenoid or mixture of carotenoids, and/or other active ingredient(s) and, optionally, an oil to the suspension as prepared in step a),
c) emulsify the mixture,
d) spray the emulsion as prepared in step c) into a bath of an aqueous solution of a calcium salt,
e) separate the formed microparticles from the bath and, optionally, wash the microparticles, and
f) optionally dry the microparticles obtained in step e).

The preparation of the aqueous pectin suspension is suitably carried out with heating, e.g., up to a temperature of about 90° C. To the pectin suspension, the active ingredient (the carotenoid and/or other physiologically active ingredient) is then added at a temperature of about 50-70° C., particularly at about 50-65° C. (step b). Emulsification (step c) is suitably carried out at the same temperature range while lower or higher temperatures, e.g. temperatures in the range of from 30-90° C. are also possible.

The ionotropic gel formation of low methoxylated pectin can be induced by cations of two or more valencies, such as Ca++, Mg++ and Al+++, especially Ca++. Thus, every sufficiently water-soluble salt of such cations, e.g., Ca-lactate, chloride dihydrate, citrate or triphosphate can be used in step d). Suitably, the concentration of the calcium salt solution is about 0.1 to about 0.6 molar. The so-obtained microparticles can be separated and, if desired, be dried by conventional means, e.g. by centrifugation (step e) or freeze-drying (step f).

The process of the invention is illustrated further in FIG. 1 as well as in the Examples.

In still another aspect, the present invention relates to food containing a composition comprising a pectin and a carotenoid or mixture of carotenoids, and/or other active ingredient(s), as defined earlier.

It has surprisingly been found that the composition as set out above is very well suitable to deliver the carotenoid (or other appropriate physiologically active ingredient) where they are desired for the purpose. Carotenoids (or other physiologically active ingredients) when encapsulated in pectin, can pass the stomach and small intestine in a mostly intact form (i.e. more than 50% of the particles remain intact) and may reach the large intestine (the colon) without substantial uptake at earlier stages of the intestinal tract. Without wishing to be bound by theory, it is believed this is due to the properties of the pectin, which is hard to digest or to break down by the human body's own enzymes. It is thought that once in the colon, however, microorganisms that are present in the colon will produce enzymes which break down the pectic material. Such enzymes may be e.g. pectin lyases and pectate lyases and polygalacturonases. It is believed that pectin is quite unique in this respect, and as an additional advantage said pectin particles are relatively easy to prepare, and pectin is considered a well-accepted functional ingredient, especially in plant-derived food preparations.

The compositions according to the invention are preferably such that a carotenoid is encapsulated by or embedded in the pectin. Such encapsulated or embedded carotenoids may be used as part of a food or dietetic composition, preferably in an aqueous composition. Examples of such liquid or viscous food compositions are fruit or vegetable juices and sauces/purees, (dietetic) fruit or vegetable drinks and (sports) drinks. Such food compositions may be prepared by adding an appropriate amount of a pectin composition to the food. Suitably, up to 1 g of a pectin composition acording to the invention is added to 1 liter of a beverage to provide about 20 mg/l of provitamin A and to achieve an appropriately intense colour of the beverage.

Preferably the composition according to invention comprise at least 1% (by weight, based on the dry weight of the total composition)) of a carotenoid or other physiologically active ingredient(s). In principle all carotenoids may be used in the compositions according to the invention. Preferred carotenoids are α-carotene, β-carotene, lycopene, astaxanthin, canthaxanthin, lutein, zeaxanthin, or mixtures thereof. Examples of other physiologically active ingredients for use in the present invention are polyunsaturated fatty acids such as arachidonic acid or docosahexaenoic acid; tocopherols such as α-tocopherol; phytosterols; and phytoestrogens. In a preferred aspect of the invention, the active ingredient is a carotenoid, especially β-carotene including its (natural) mixtures with other carotenes.

The compositions according to the invention may comprise further ingredients such as (vegetable or essential) oils in which the carotenoid (or other physiologically active ingredient) may be dispersed or partly or completely dissolved. In such compositions the carotenoid may be dispersed in oil at a ratio (by weight) of carotenoid:oil between 1:500 and 1:2.

Further additional ingredients may be compounds also exhibiting beneficial effects in the colon and which may prevent the stomach and small intestine from irritation and which should pass the stomach and small intestine without breakdown or digestion, respectively, or may be components that help stabilise the composition, e.g. antioxidants, or components that are found together with carotenoids. A preferred antioxidant is α-tocopherol, e.g. in an amount of 0.01-5% by weight.

Compared to gelatin-based compositions, the use of pectin as encapsulating material according to the invention provides a further benefit when applied as an additive in fruit/vegetable juices or fruit/vegetable drinks with high fruit contents. Fruits contain a range of polyphenols, which in the presence of protein (e.g. gelatin) may interact to form a deposit of cloud, resulting in unattractive products. The use of pectin-based carotene compositions avoids protein-polyphenol-reactions and may therefore be suitable for producing attractive juices and drinks.

The invention is illustrated further by the Examples which follow.

EXAMPLE 1

Preparation of β-Carotene-Containing Microcapsules

For preparation of dry β-carotene-containing microcapsules a process was followed as shown in FIG. 1.

2 kg of an aqueous suspension of 3% (by weight) of low methoxylated pectin ("Pektin Classic AU-L 062/00" as obtainable from Herbstreith & Fox, D-75305 Neuenbürg, Germany) was prepared at 80° C. using an Ultraturrax at 20.0000 rpm. To this suspension, 15 ml of a 30% dispersion of β-carotene in vegetable oil were added at a temperature of 55° C. under stirring, and the mixture was emulsified in an in-line Turrax at 15.000 rpm. The so-obtained emulsion was then sprayed into a 0.1 m calcium chloride solution. The formed microgel particles were separated using a centrifuge. After washing, the particles were freeze-dried to yield a red-coloured powder containing ca. 2% by weight of β-carotene. Particle size: 60% by weight had a size between 1 and 50 micron.

Sustained release of the active ingredient was tested by incubation of the microparticles with artificial gastric juice and with pectolytic enzymes at 35° C., and quantified by HPLC as described by MARX et al. (2000): *Food Chemistry* 70, pp. 403-408.

EXAMPLE 2

β-Carotene-Fortified Orange Juice

Using the dried particles as prepared following example 1, a fortified orange juice may be prepared which contains 0.2-0.5 mg β-carotene 100 ml to intensify the natural orange colour of the juice.

Particle sizes are preferably below 5 micron.

EXAMPLE 3

β-Carotene-Fortified Fruit Drink

An apple juice drink Ouice content 25%) with up to 1 mg of carotene/100 ml drink may be prepared using the dried particles as prepared following example 1.

This may be achieved by mixing the dried particles according to the invention (particle size preferably less than 5 micron) with water, sugar syrup, apple juice concentrate, lemon juice, ascorbic acid, and aromas. This mixture may be homogenised, pasteurised, degassed, filled into bottles and cooled. When kept in the dark at room temperature, no substantial undesired deposit will be formed within 12 months.

In this case the particles are used to yield both a colouring and a nutritional benefit. After ingestion of this drink, the pectin wall of the particles will be broken down by the colon microflora and the carotene content will be released.

What is claimed is:

1. An edible composition consisting of:
   at least 25% by weight (based on the dry weight of the total composition) of a pectin, excluding beet pectin, wherein the pectin has a degree of esterification (DE) below 50% and gelatinizes by ionotropic gel formation, and, encapsulated in the pectin is
   at least 0.2% by weight (based on the dry weight of the total composition) of a carotenoid selected from the group consisting of α-carotene, β-carotene, lycopene, astaxanthin, canthaxanthin, lutein, zeaxanthin, and mixtures thereof as an active ingredient, and
   0.01-5% by weight (based on the dry weight of the total composition) of an antioxidant,
   wherein most of the carotenoid encapsulated in the pectin remains intact and passes the stomach and intestine.

2. The edible composition according to claim 1, wherein more than 50% of the carotenoid encapsulated in the pectin remains intact and passes the stomach and intestine.

3. The edible composition according to claim 1, wherein the pectin is apple pectin or citrus pectin or a mixture thereof.

4. The edible composition according to claim 1, comprising at least 1% by weight (based on the dry weight of the total composition) of a carotenoid.

5. The edible composition according to claim 1, wherein the antioxidant is α-tocopherol.

6. The edible composition according to claim 1, wherein the carotenoid is dispersed in oil at a ratio (by weight) of carotenoid:oil between 1:500 and 1:2.

7. The edible composition according to claim 1, wherein the carotenoid is completely or partly dissolved in oil at ratio (by weight) of carotenoid:oil between 1:1000 and 1:5.

8. A food comprising a composition according to claim 1.

9. The food according to claim 8, which is a fruit juice or vegetable juice, sauce/puree, (dietetic) fruit or vegetable drink or (sports) drink.

10. An edible composition consisting of:
    at least 25% by weight (based on the dry weight of the total composition) of a pectin, excluding beet pectin, wherein the pectin has a degree of esterification (DE) below 50% and gelatinizes by ionotropic gel formation, and, encapsulated in the pectin is
    at least 0.2% by weight (based on the dry weight of the total composition) of a carotenoid selected from the group consisting of α-carotene, β-carotene, lycopene, astaxanthin, canthaxanthin, lutein, zeaxanthin, and mixtures thereof as an active ingredient and,
    0.01-5% by weight (based on the dry weight of the total composition) of an antioxidant,
    optionally the carotenoid is dispersed in an oil, wherein most of the carotenoid encapsulated in the pectin remains intact and passes the stomach and intestine.

\* \* \* \* \*